United States Patent
Urushiya et al.

(10) Patent No.: US 8,249,216 B2
(45) Date of Patent: Aug. 21, 2012

(54) X-RAY MOVING IMAGE RADIOGRAPHING APPARATUS

(75) Inventors: Hiroyuki Urushiya, Saitama (JP); Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/421,120

(22) Filed: Apr. 9, 2009

(65) Prior Publication Data
US 2009/0257559 A1    Oct. 15, 2009

(30) Foreign Application Priority Data

Apr. 14, 2008    (JP) .................................. 2008-104300

(51) Int. Cl.
H05G 1/70    (2006.01)
H05G 1/10    (2006.01)
H05G 1/60    (2006.01)

(52) U.S. Cl. ......... 378/92; 378/95; 378/98.6; 378/98.11
(58) Field of Classification Search .................... 378/93, 378/98.6, 92, 95, 98.11
See application file for complete search history.

(56) References Cited

U.S. PATENT DOCUMENTS

| | | | | |
|---|---|---|---|---|
| 4,147,935 A | * | 4/1979 | Warrikhoff | 378/98.6 |
| 4,247,780 A | * | 1/1981 | Webber et al. | 378/98.6 |
| 4,544,949 A | * | 10/1985 | Kurihara | 378/98.12 |
| 4,692,864 A | * | 9/1987 | Shimoni et al. | 600/443 |
| 5,123,056 A | * | 6/1992 | Wilson | 382/132 |
| 5,490,197 A | * | 2/1996 | Albert et al. | 378/113 |
| 5,594,770 A | * | 1/1997 | Bowles et al. | 378/58 |
| 5,859,893 A | * | 1/1999 | Moorman et al. | 378/154 |
| 6,236,709 B1 | * | 5/2001 | Perry et al. | 378/57 |
| 6,292,531 B1 | * | 9/2001 | Hsieh | 378/37 |
| 6,483,890 B1 | * | 11/2002 | Malamud | 378/22 |
| 7,187,748 B2 | * | 3/2007 | Hoffman | 378/15 |
| 7,313,214 B2 | * | 12/2007 | Bruder et al. | 378/15 |
| 7,330,529 B2 | * | 2/2008 | Kautzer et al. | 378/37 |
| 7,432,924 B2 | * | 10/2008 | Ohishi | 345/419 |
| 7,526,065 B2 | * | 4/2009 | Hardesty | 378/62 |
| 7,724,875 B2 | * | 5/2010 | Jabri et al. | 378/98.9 |
| 7,746,974 B2 | * | 6/2010 | Shukla | 378/4 |
| 7,885,375 B2 | * | 2/2011 | Bernard De Man et al. | 378/9 |
| 2009/0022264 A1 | * | 1/2009 | Zhou et al. | 378/5 |

* cited by examiner

*Primary Examiner* — Thomas R Artman
(74) *Attorney, Agent, or Firm* — Canon U.S.A., Inc. IP Division

(57) ABSTRACT

An X-ray moving image radiographing apparatus includes an X-ray detector configured to detect an X-ray transmitting through a subject to acquire a subject image, an image processing unit configured to process an X-ray radiographic image output from the X-ray detector, and a control unit configured to capture a mask image by selectively scanning X-ray focal positions of an X-ray source which has a plurality of X-ray focal points so that an X-ray incident angle varies with respect to a target point of the subject, and to capture a moving image after a predetermined work is performed on the subject by selectively scanning X-ray focal positions of the X-ray source similar to the scanning operation used to capture the mask image.

21 Claims, 6 Drawing Sheets

X-RAY MOVING IMAGE RADIOGRAPHING APPARATUS

BACKGROUND OF THE INVENTION

1. Field of the Invention

The present invention relates to an X-ray moving image radiographing apparatus that captures X-ray radiographic images while a medical professional is providing treatment with respect to a subject.

2. Description of the Related Art

Recently, a technique of Digital Subtraction Angiography (DSA) imaging has become widely used in angiography imaging. DSA imaging is an X-ray radiographing method wherein an X-ray radiographic image is captured before injection of a contrast medium to form a mask image. An X-ray radiographic image is captured after injecting the contrast medium into a blood vessel of a subject, and a background is removed by subtracting the mask image from the contrast medium-injected X-ray radiographic image. Thus, an image of blood vessels to which the contrast medium was injected can be displayed.

An important aspect of DSA imaging is to comprehend a running state of blood vessels. The blood vessels within a human body reside in a three-dimensional space. However, when the blood vessels are subjected to the X-ray radioscopic imaging, information about the blood vessels is compressed into two-dimensional information from three-dimensional information. Consequently, it is difficult to accurately comprehend a running state of the complicated blood vessels by observing a simpler two-dimensional image.

To comprehend the running state of the blood vessel in a three-dimensional manner, a technique of rotation DSA imaging is developed. In rotation DSA imaging, an X-ray radiographic image is captured by an X-ray radiographing apparatus having an X-ray detector. The X-ray detector includes, for example, a C-shaped arm that has an X-ray source disposed on one end and an image intensifier or a flat panel detector (FPD) on the other end. The X-ray radiographing apparatus captures X-ray radiographic images by rotating the C-shaped arm around the subject, to form mask images for every one of rotation angles. After injecting a contrast medium into a blood vessel of the subject, the X-ray radiographing apparatus captures further X-ray radiographic images at the same rotational angles as those used in forming the mask images. Finally, the X-ray radiographing apparatus subtracts the mask images from the X-ray radiographic images of the corresponding rotational angles captured after injection of the contrast medium. Accordingly, moving images of only the blood vessels specified by the contrast medium can be displayed.

Further, in the angiography imaging, when the contrast medium is injected into the blood vessel of the subject, the contrast medium spreads over a wide area at high speed, so that relatively large X-ray detector is required in order to completely capture images of the spreading condition of the contrast medium. Also, it is required to continuously irradiate an X-ray over the entire area where the contrast medium is spreading.

Furthermore, for X-ray radioscopic imaging performed by a catheter or an endoscope, it is may be required to capture images to irradiate the X-ray over a wider area than an area where the catheter or the endoscope is operated.

In addition to the above described X-ray radiographic imaging method, Japanese Patent Application Laid-Open No. 06-217964 discusses a technique relating to an X-ray radiographing apparatus that electronically performs raster scanning in order to detect a focal position of the X-ray.

However, in the rotation DSA imaging, the C-shaped arm needs to be rotated at each time the mask images are captured and the angiography imaging is performed. Since the C-shaped arm is mechanically rotated, an operator must rotate the C-shaped arm with precision. More specifically, the operator needs to pay attention to the C-shaped arm to prevent the arm from striking a table or anything around the C-shaped arm, which may further complicate capturing images. Further, in the angiography imaging, the X-ray is continuously irradiated onto the entire area where the contrast medium is spreading after the injection of the contrast medium, so that X-ray irradiation dosage of the subject is extremely large as well as that of the operator who captures the images. Also, in the X-ray radioscopic imaging using the catheter or the endoscope, the X-ray irradiation dosage of the subject and the operator is extremely large.

SUMMARY OF THE INVENTION

According to an aspect of the present invention, an X-ray moving image radiographing apparatus includes an X-ray detector configured to detect an X-ray transmitting through a subject to acquire a subject image, an image processing unit configured to process an X-ray radiographic image output from the X-ray detector, and a control unit configured to capture a mask image by selectively scanning X-ray focal positions of an X-ray source which has a plurality of X-ray focal points so that an X-ray incident angle varies with respect to a target point of the subject, and to capture a moving image after a predetermined work is performed on the subject by selectively scanning X-ray focal positions of the X-ray source similar to the scanning operation used to capture the mask image.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DETAILED DESCRIPTION OF THE EMBODIMENTS

Various exemplary embodiments, features, and aspects of the invention will be described in detail below with reference to the drawings.

Figure 1:
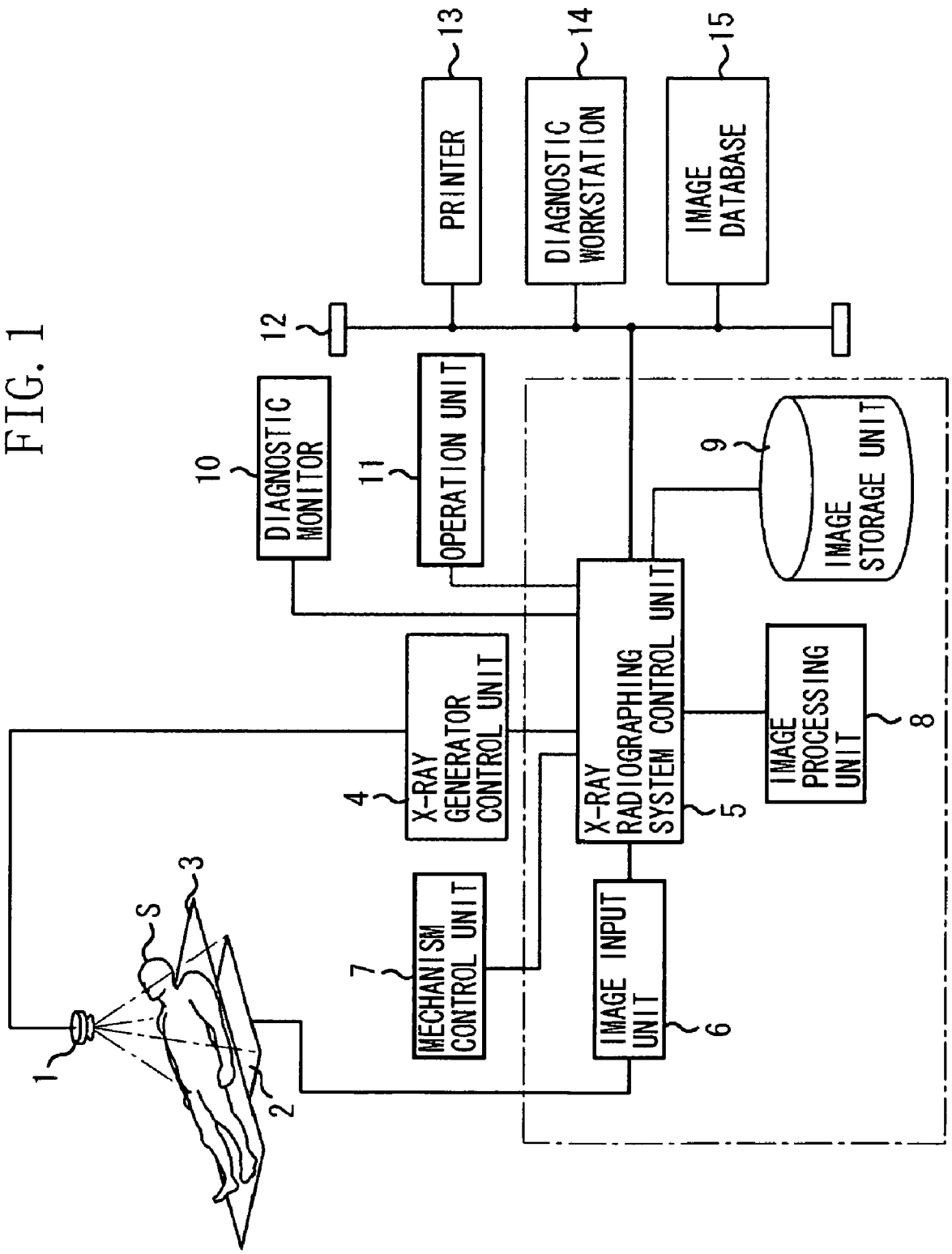
FIG. 1 is a block diagram illustrating an X-ray moving image radiographing system according to an exemplary embodiment of the present invention.

FIG. 1 is a block diagram illustrating an example of an X-ray moving image radiographing system according to an exemplary embodiment of the present invention. In the X-ray moving image radiographing system, an X-ray source 1 which generates an X-ray and an X-ray detector 2 which detects the X-ray generated from the X-ray source 1 are arranged to face each other. Further, a table 3 on which a subject S lies down is arranged between the X-ray source 1 and the X-ray detector 2. As described below, the X-ray source 1 is provided with a lead diaphragm 1a, and the X-ray detector 2 is provided with a grid 2a.

The X-ray source 1 is connected to an output of an X-ray radiographing system control unit 5 via an X-ray generator unit control unit 4 which controls generation of an X-ray. An output of the X-ray detector 2 is connected to the X-ray radiographing system control unit 5 via an image input unit 6. The X-ray radiographing system control unit 5 is connected to a mechanism control unit 7 which controls a mechanism of the system, an image processing unit 8 which processes images, an image storage unit 9 which stores images, a diagnostic monitor 10 which displays images, and an operation unit 11 which performs various operations. Further, the X-ray radiographing system control unit 5 is connected to an external printer 13, a diagnostic workstation 14, and an image database 15 via a network 12.

The X-ray generated from the X-ray source 1 which is controlled by the X-ray generator unit control unit 4, transmits through the subject S and is detected by the X-ray detector 2 as a subject image. The detected X-ray radiographic image is input into the X-ray radiographing system control unit 5 as image data via the image input unit 6. The image data is subjected to image processing such as correction of the X-ray detector 2, preprocessing including log conversion, noise removal, sharpening, and image quality enhancement processing such as dynamic range compression, and an image analysis in the image processing unit 8.

The image having been subjected to image processing is displayed on the diagnostic monitor 10. For the moving image radiography, the image processing is continuously repeated to capture images in chronological order and the captured images are continuously displayed on the diagnostic monitor 10. Further, the images captured in chronological order are stored in the image storage unit 9, or output to the printer 13, the diagnostic workstation 14, and the image database 15 via the network 12.

Figure 2:
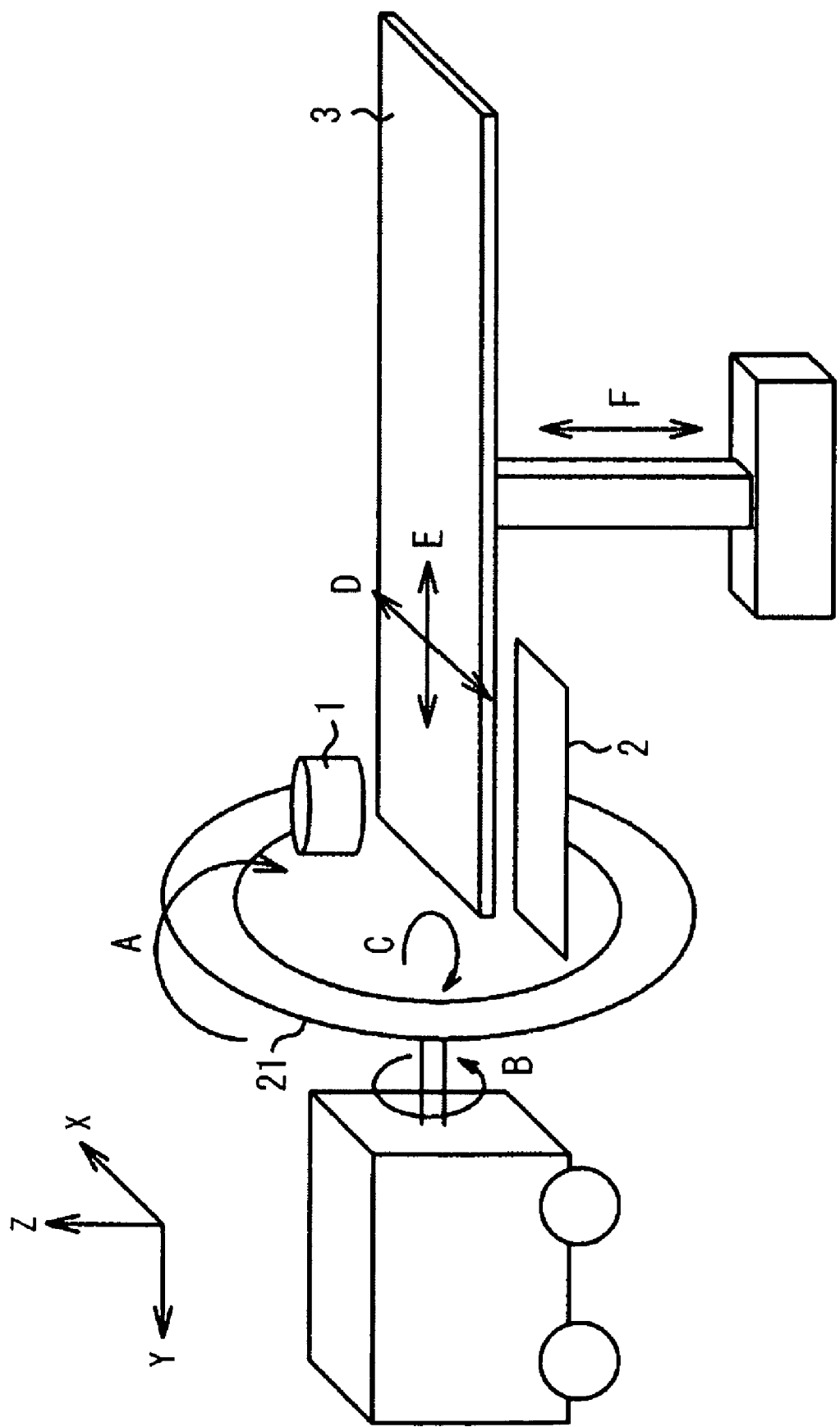
FIG. 2 is a configuration diagram of a C-shaped arm.

FIG. 2 is a configuration diagram of a C-shaped arm, as a retaining mechanism to retain the X-ray source 1 and the X-ray detector 2. On both ends of the C-shaped arm 21, the X-ray source 1 and the X-ray detector 2 are fixed. The C-shaped arm 21 can rotate in three directions, i.e., directions of X axis, Y axis, and Z axis which are indicated by arrows A, B, and C. The table 3 can also move interlockingly with the C-shaped arm 21 in three directions, i.e., directions of front-to-rear, right-to-left, and up-and-down which are indicated by arrows D, E, and F.

The table 3 and the C-shaped arm 21 are controlled by the mechanism control unit 7 to capture images of the subject S in any directions and at any positions, which is not illustrated in FIG. 2.

Figure 3A:
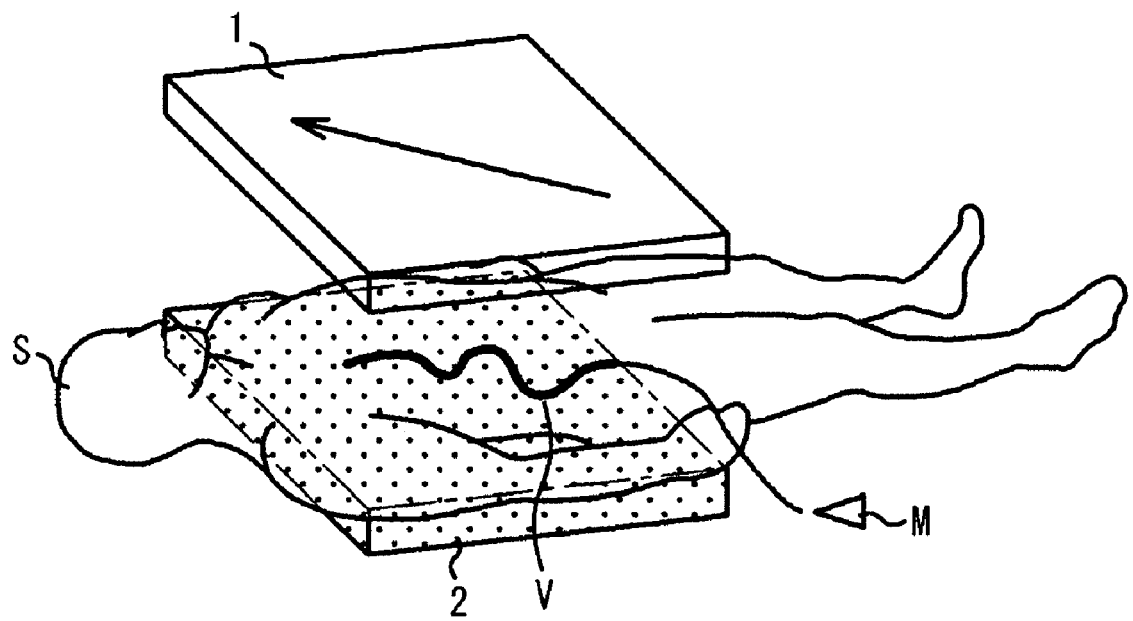
FIGS. 3A and 3B illustrate how to capture images according to angiography imaging.
Figure 3B:
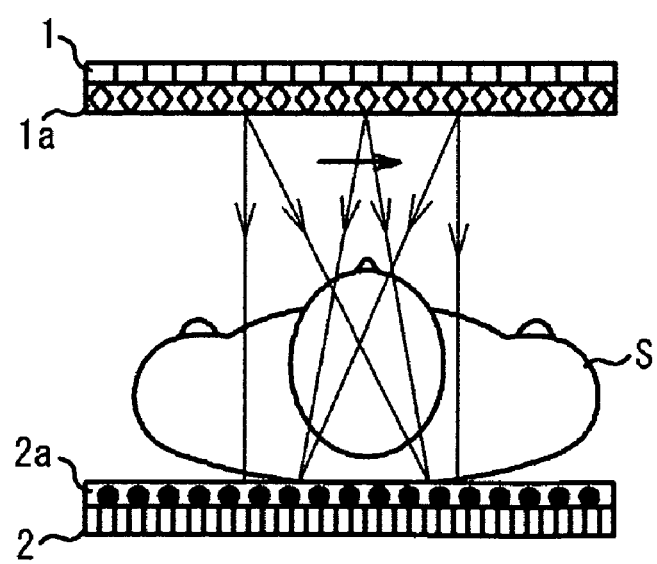

By using the above described X-ray moving image radiographing system, the rotation DSA imaging and the X-ray radioscopic imaging using the catheter or the endoscope are performed. In the rotation DSA imaging, the mask images are captured before injecting a contrast medium. Conventionally, the images are captured while the C-shaped arm 21 is rotated in an A direction or a B direction as illustrated in FIG. 2. However, according to the present exemplary embodiment, once the C-shaped arm 21 is moved and positioned at the beginning, X-ray focal positions are scanned in an area where the contrast medium is expected to spread over in a predetermined direction, as illustrated in FIG. 3A, without driving the C-shaped arm 21 during the image capturing process. FIG. 3B is a cross sectional view of the above processing from a head of the subject S.

In the X-ray source 1, the X-ray focal points of a number of N×M are arranged on a plane surface which is sectioned by the lead diaphragm 1a. By selectively scanning these X-ray focal points in the above described direction, an X-ray irradiation result similar to that of the X-ray irradiation with driving the C-shaped arm 21 can be obtained. The image of every X-ray focal position can be captured by using the X-ray detector 2 having a grid 2a during a scanning operation of the X-ray focal positions. The captured images are referred to as mask images.

After capturing the mask images, a contrast medium M is injected into a blood vessel V of the subject S. When the contrast medium M circulates around the blood vessel V, the X-ray focal positions are scanned to capture images according to a method as in the case of forming the mask images. At the time, the prior mask images are respectively accorded with the corresponding images which were captured at the same X-ray focal positions, and are subtracted therefrom to remove unnecessary background. Accordingly, a moving image of only the blood vessel V specified with the contrast medium M can be obtained. Further, since the X-ray focal positions change, the blood vessel V specified with the contrast medium M can be observed from a variety of X-ray incident angles by continuously displaying the subtracted images as the X-ray focal positions are scanned. Accordingly, a running state of the complicated bloods vessels V, a lump and constriction on the blood vessels V, or the like, can be accurately comprehended in three dimensions. Energy of X-ray to be irradiated for capturing the mask images may be different from energy of X-ray to be irradiated for capturing images after the contrast medium M is injected into the blood vessel V. The X-ray moving image radiographing apparatus can capture images through DSA imaging without involving any mechanical actions after being positioned at the beginning. To assist scanning of the X-ray focal points, the C-shaped arm 21 may also be optionally moved.

Figure 4A:
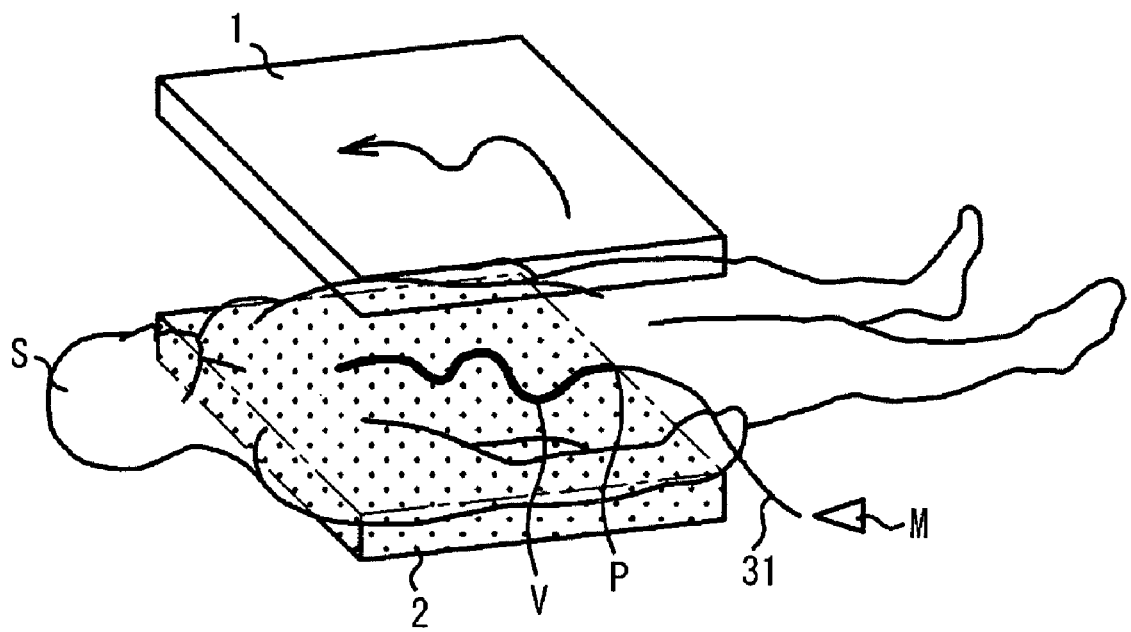
FIGS. 4A and 4B illustrate how to capture images according to catheter imaging.
Figure 4B:
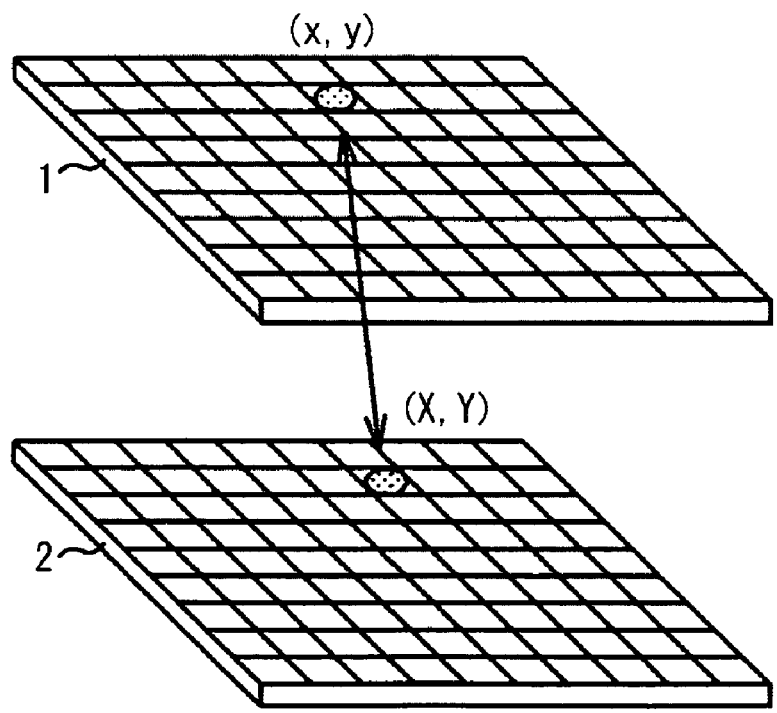

In a second exemplary embodiment, the X-ray radioscopic imaging is performed by using the catheter or the endoscope. FIG. 4A illustrates how to capture images by using the catheter. In FIG. 4A, a catheter 31 is initially inserted into the blood vessel V of the subject S to get the catheter 31 to reach a target position P. At the time, the X-ray focal positions are selected to move so as to trace a top end of the catheter 31. As illustrated in FIG. 4B, the X-ray source 1 and the X-ray detector 2 are arranged to face each other and each of the X-ray focal positions of the X-ray source 1 is given a coordinate of (x, y) and each of pixel positions of the X-ray detector 2 is given a coordinate of (X, Y). Correspondence relationships between the coordinates (X, Y) and the coordinates (x, y) which are spatially closest to each other are made into a table.

Accordingly, a position of the top end of the catheter 31 is determined from an X-ray radiographic image. In order to determine the position of the top end of the catheter 31, the immediately preceding image is subtracted from each of the images in chronological order, and a portion where the top end of the catheter 31 moves is extracted to find a coordinate of the portion.

When the coordinate of the position of the top end of the catheter 31, namely a positional coordinate in the X-ray detector 2 is determined, a coordinate of the X-ray focal position of the X-ray source 1 corresponding to the position of the top end of the catheter 31 can be acquired from the above described table of correspondence relationships. Then, the X-ray irradiation can trace the top end of the catheter 31 by selectively irradiating the X-ray onto the X-ray focal position.

When the catheter 31 reaches the target position, the contrast medium M is injected from the other end of the catheter 31. The injected contrast medium M spreads over the peripheral blood vessels V. The injected contrast medium M spreads not only in a single blood vessel V, but also spreads over branches of the blood vessel V. The X-ray is irradiated from the X-ray focal position corresponding to a center position of the whole blood vessels where the contrast medium M is spreading over. At the center position of the whole blood vessels V, the immediately preceding image is subtracted from each of the images captured in chronological order, as is the case of the top end of the catheter 31. Here, there are differences that are dispersed in a plurality of positions. Therefore, a center of the dispersed positions is calculated to make it the X-ray focal position.

As described above, the X-ray is irradiated from the sequentially determined X-ray focal positions and X-ray radiographic images can be obtained based on moving images captured by tracing the contrast medium M that is spreading over the blood vessels V. If it is so configured that the X-ray focal positions, as target points selected after insertion of the catheter 31 or after injection of the contrast medium M, are continuously selected, the X-ray can be irradiated over an entirety of the inserted catheter 31 and the whole blood vessels V specified by the contrast medium M.

Figure 5:
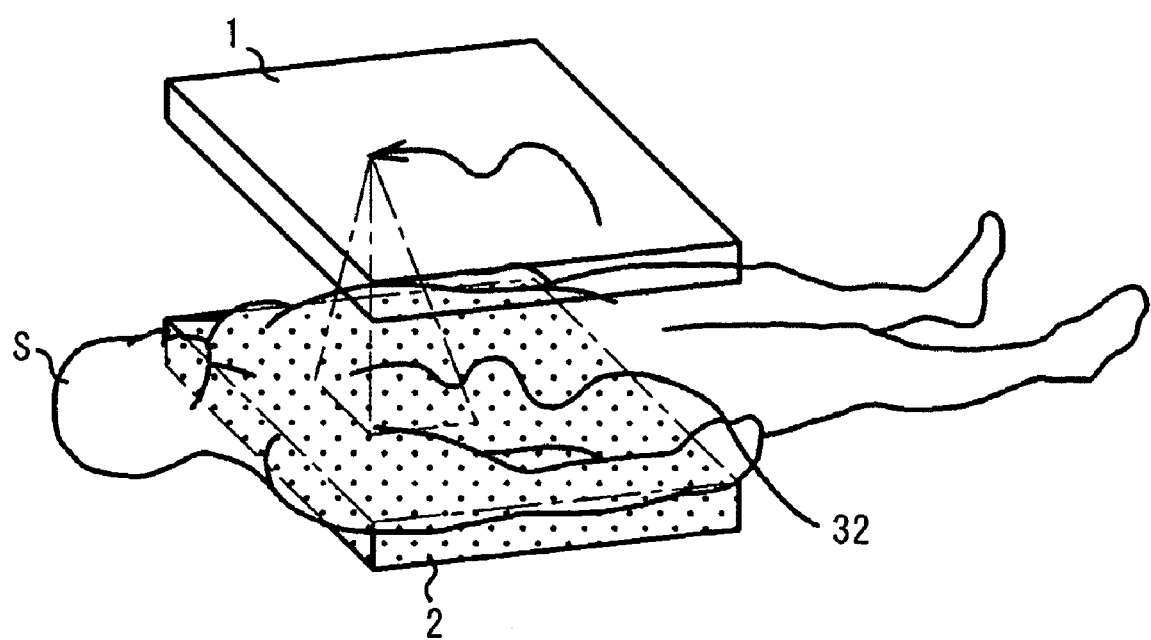
FIG. 5 illustrates how to capture images according to endoscope imaging.

FIG. 5 illustrates how to capture images by operating an endoscope according to a third exemplary embodiment. In the case of operating an endoscope 32, as in the case of using the catheter 31 according to the second exemplary embodiment, a top end of the endoscope 32 is traced and the X-ray is irradiated to the subject by varying the X-ray focal positions.

In the third exemplary embodiment, a technique of energy subtraction is used in capturing the X-ray moving images in addition to what is described in the first and second exemplary embodiments. In the energy subtraction, energy of X-ray to be irradiated is varied by changing a tube voltage, the energy-varied X-ray is irradiated twice, and an image is formed according to a difference between the irradiations. The energy subtraction utilizes a property that materials have different X-ray absorption ratios according to the difference of energy. Therefore, the energy subtraction can provide a better image than a normal image that is captured when the X-ray is irradiated only once.

With the above described method, the energy subtraction X-ray radioscopic imaging can be performed by switching a degree of energy for each X-ray irradiation, irradiating the X-ray twice, and calculating the difference thereof.

Figure 6:
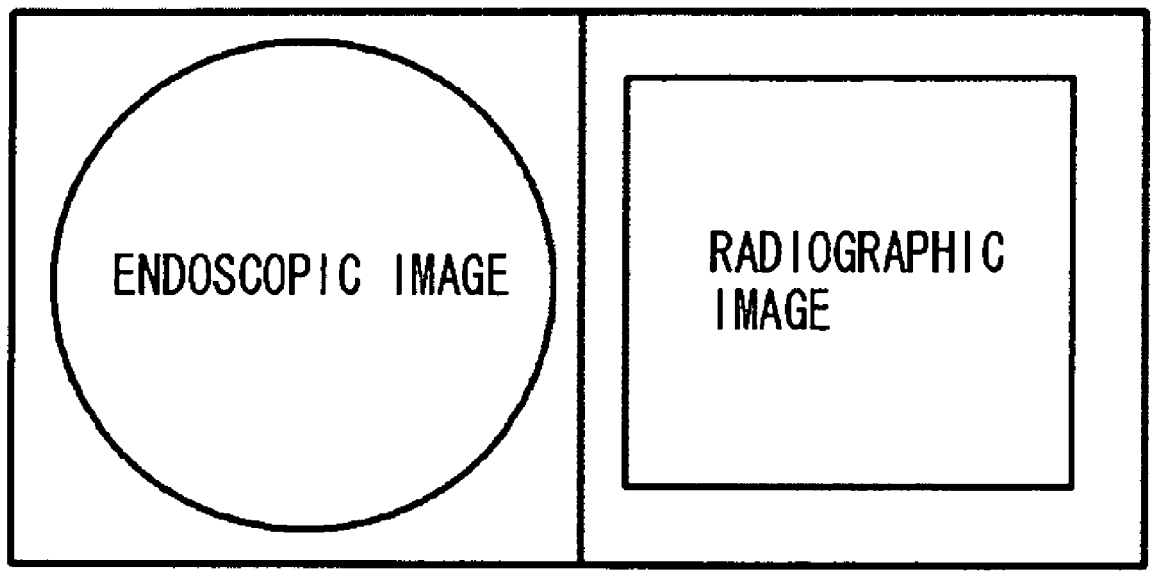
FIG. 6 illustrates a screen of a diagnostic diagnosis.

In the third exemplary embodiment, since the endoscope 32 is inserted into a body of the subject S, a positional relationship between a position of the body and an inside of the body can be effectively comprehended by displaying moving images of the endoscope on the diagnostic monitor 10 together with the X-ray moving images in a manner illustrated in FIG. 6.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-104300 filed on Apr. 14, 2008, which is hereby incorporated by reference herein in its entirety.

What is claimed is:

1. An X-ray image radiographing apparatus comprising:
   an X-ray detector, having a two-dimensional detection area, configured to detect X-ray radiation transmitting through a subject to acquire an X-ray radiographic image; and
   an X-ray source having a plurality of X-ray focal points configured to emit a cone-beam X-ray onto the X-ray detector whose detecting areas in the two-dimensional detection area that correspond to at least two of the X-ray focal points are different; and
   a control unit configured to select an X-ray focal point corresponding to a change in the subject and control the X-ray source to irradiate the subject with an X-ray from a selected X-ray focal point.

2. The X-ray image radiographing apparatus according to claim 1, wherein the control unit selects the X-ray focal point so that the X-ray incident angle of the cone-beam X-ray varies with respect to a target point of the subject and irradiates the subject with the X-ray from the selected X-ray focal point after a predetermined work is performed on the subject.

3. The X-ray image radiographing apparatus according to claim 2, wherein the predetermined work is one of injection of a contrast medium, insertion of a catheter, and insertion of an endoscope to the subject.

4. The X-ray image radiographing apparatus according to claim 2, further comprising:
   a image processing unit configured to acquire a first X-ray radiographic image before the predetermined work is performed, acquire a second X-ray radiographic image after the predetermined work is performed, and subtract the first X-ray radiographic image from the second X-ray radiographic image to generate a subtraction image,
   wherein the control unit selects the X-ray focal point based on the subtraction image, and
   wherein the predetermined work is one of an injection of a contrast medium, an insertion of a catheter and an insertion of an endoscope.

5. The X-ray image radiographing apparatus according to claim 1, wherein the control unit extracts a movement of a target point of the subject from the X-ray radiographic image acquired by the X-ray detector and determines the target point from the extracted movement.

6. The X-ray image radiographing apparatus according to claim 1, wherein the control unit stores a correspondence relationship between the X-ray radiographic image acquired by the X-ray detector and the X-ray focal position in a table and determines the X-ray focal position based on the X-ray radiographic image by using the table.

7. The X-ray image radiographing apparatus according to claim 1, wherein the control unit selects the X-ray focal point from the plurality of X-ray focal points and controls the X-ray source to irradiate the subject with an X-ray from the selected X-ray focal point.

8. The X-ray image radiographing apparatus according to claim 1, wherein the control unit specifies the change in the subject based on the X-ray radiographic image.

9. The X-ray image radiographing apparatus according to claim 1,
   wherein the control unit sequentially determines a target point of the subject based on the change of the X-ray radiographic image acquired by the X-ray detector, sequentially selects X-ray focal points with respect to the target point and irradiates the subject with an X-ray from a selected X-ray focal point.

10. The X-ray image radiographing apparatus according to claim 9,
wherein the control unit determines one of a top end of a catheter in a blood vessel and a top end of an endoscope as the target point of the subject based on the change in the X-ray radiographic image, and selects an X-ray focal point with respect to the target point.

11. The X-ray image radiographing apparatus according to claim 9,
wherein the control unit determines a top end of an endoscope as the target point of the subject based the a change in the X-ray radiographic image, selects an X-ray focal point with respect to the target point, and displays the X-ray radiographic image and the image obtained by the endoscope.

12. The X-ray image radiographing apparatus according to claim 1, further comprising:
an image processing unit configured to generate an energy subtraction image from two X-ray radiographic images for which two irradiations are different in X-ray energy,
wherein the control unit selects the X-ray focal point based on the energy subtraction image.

13. The X-ray image radiographing apparatus according to claim 1,
wherein the control unit acquires, based on the change in the subject, a region where contrast medium is, and selects a plurality of focal points corresponding to the region.

14. The X-ray image radiographing apparatus according to claim 1,
wherein the control unit acquires, based on the change in the subject, a vessel region where contrast medium is injected, and selects a plurality of focal points along with the vessel region.

15. A non-transitory computer-readable storage medium storing a computer program of instructions which cause a computer to perform a method comprising:
irradiating a target point of a subject with X-ray radiation emitted by a radiation source, the radiation source having a plurality of X-ray focal points configured to emit a cone-beam X-ray onto an X-ray detector;
acquiring an X-ray radiographic image of the subject from the X-ray detector, wherein cone-beams of at least two of the X-ray focal points of the radiation source are detected at different areas of the X-ray detector;
processing the detected X-ray radiographic image;
selecting an X-ray focal point corresponding to a change in the subject; and
controlling the X-ray source to irradiate the target point of the subject with an X-ray from the selected X-ray focal point.

16. A control apparatus for controlling an X-ray source having a plurality of X-ray focal points comprising:
an input unit configured to acquire an X-ray image from a detector which detects an X-ray being generated by the X-ray source and transmitting through a subject; and
a control unit configured to select only one X-ray focal point from the plurality of X-ray focal points based on a change of the subject, and to control the X-ray source to irradiate the subject with the X-ray from the selected X-ray focal point.

17. A control apparatus for controlling an X-ray source having a plurality of X-ray focal points comprising:
an input unit configured to acquire an X-ray image from a detector which detects an X-ray being presented by the X-ray source and transmitting through a subject; and
a control unit configured to extract an area the subject moves by calculating a subtraction of the plurality of X-ray images, determine a target point in the X-ray image from the area, select an X-ray focal point corresponding to the position of the determined target points from the plurality of X-ray focal point, and control the X-ray source to irradiate the subject with the X-ray from the selected X-ray focal point, wherein the control unit displays on a display unit the X-ray images as a moving image, each from of the moving image corresponding to one unit focal point.

18. A method for controlling an X-ray source having a plurality of X-ray focal points, the method comprising:
acquiring an X-ray image from a detector which detects an X-ray being generated by the X-ray source and transmitting through a subject;
selecting only one X-ray focal point from the plurality of X-ray focal points according to a change in the subject; and
irradiating the subject with the X-ray from the selected X-ray focal point.

19. A method for controlling an X-ray source having a plurality of X-ray focal points comprising:
acquiring an X-ray image from a detector which detects an X-ray being generated by the X-ray source and transmitting through a subject;
extracting an area where the subject moves by calculating a subtraction of the plurality of X-ray images;
determining a target point in the X-ray image from the area;
selecting an X-ray focal point corresponding to the position of the determined target point from the plurality of X-ray focal points;
irradiating the subject with the X-ray from the selected X-ray focal point, and
displaying on a display unit the X-ray images as a moving image, each frame of the moving image corresponding to one unique focal point.

20. An X-ray image radiographing apparatus comprising:
an X-ray detector configured to detect an X-ray transmitting through a subject to acquire an X-ray radiographic image; and
a control unit configured to select only one X-ray focal point corresponding to a change in the subject and control an X-ray source to irradiate the subject with an X-ray from a selected X-ray focal point.

21. An X-ray image radiographing apparatus comprising:
an X-ray detector configured to detect an X-ray transmitting through a subject to acquire an X-ray radiographic image; and
a control unit configured to select an X-ray focal point corresponding to a change in the subject and control an X-ray source to irradiate the subject with an X-ray from a selected X-ray focal point,
wherein the control unit displays on a display unit the X-ray images as a moving image, each frame of the moving image corresponding to one unique focal point.

* * * * *